(12) United States Patent
Yamataka et al.

(10) Patent No.: US 9,526,448 B2
(45) Date of Patent: Dec. 27, 2016

(54) STATE ESTIMATION DEVICE AND STATE ESTIMATION PROGRAM

(71) Applicant: DENSO CORPORATION, Kariya, Aichi-pref. (JP)

(72) Inventors: Minori Yamataka, Nisshin (JP); Takeshi Enya, Nagoya (JP); Hiroyuki Kishita, Kariya (JP)

(73) Assignee: DENSO CORPORATION, Kariya (JP)

( * ) Notice: Subject to any disclaimer, the term of this patent is extended or adjusted under 35 U.S.C. 154(b) by 157 days.

(21) Appl. No.: 14/519,430

(22) Filed: Oct. 21, 2014

(65) Prior Publication Data

US 2015/0173665 A1 Jun. 25, 2015

(30) Foreign Application Priority Data

Dec. 19, 2013 (JP) .................. 2013-262543

(51) Int. Cl.
*A61B 3/14* (2006.01)
*A61B 5/18* (2006.01)
*A61B 3/113* (2006.01)
*A61B 5/00* (2006.01)
*B60K 28/06* (2006.01)
*A61B 5/16* (2006.01)

(52) U.S. Cl.
CPC .................. *A61B 5/18* (2013.01); *A61B 3/113* (2013.01); *A61B 5/6893* (2013.01); *B60K 28/066* (2013.01); *A61B 5/165* (2013.01)

(58) Field of Classification Search
CPC ....................................................... A61B 3/113
USPC ................................................. 351/209, 210
See application file for complete search history.

(56) References Cited

U.S. PATENT DOCUMENTS

| | | | |
|---|---|---|---|
| 7,455,405 B2 * | 11/2008 | Victor ................... | A61B 3/036 351/200 |
| 2010/0191156 A1 | 7/2010 | Sakamoto et al. | |
| 2011/0178784 A1 * | 7/2011 | Sato ..................... | A61B 5/0496 703/2 |

OTHER PUBLICATIONS

Kakizaki et al. (2013) "Study on Detection of Driver Attention Using Microsaccades", 2013 JSAE Annual Congress (Autumn).

* cited by examiner

*Primary Examiner* — Huy K Mai
(74) *Attorney, Agent, or Firm* — Posz Law Group, PLC (57) ABSTRACT

According to the present disclosure, a state estimation device estimating a state of a monitoring target based on an involuntary eye movement of an eyeball of the monitoring target is provided. The state estimation device in the present disclosure includes a microsaccade information acquisition portion obtaining microsaccade information that includes a state of variation of a gaze angle when a microsaccade of the involuntary eye movement occurs, and a state estimation portion estimating the state of the monitoring target based on the microsaccade information.

18 Claims, 7 Drawing Sheets

STATE ESTIMATION DEVICE AND STATE ESTIMATION PROGRAM

CROSS REFERENCE TO RELATED APPLICATION

This application is based on Japanese Patent Application No. 2013-262543 filed on Dec. 19, 2013, the disclosure of which is incorporated herein by reference.

TECHNICAL FIELD

The present disclosure relates to a state estimation device and a state estimation program, which estimates a state of a monitoring target.

BACKGROUND ART

Patent literature 1: US 2010/0191156 A1 (corresponding to Japanese Patent No. 5302193 and WO 2009/001558)

For example, patent literature 1 discloses a state estimation device, which monitors an involuntary eye movement of a monitoring target and estimates a state of the monitoring target according to whether an occurrence frequency of the involuntary eye movement is matched with a database.

The inventors of the present disclosure have found the following.

The conventional state estimation device may require a period of time for several tens of seconds before an occurrence frequency of the involuntary eye movement is detected.

SUMMARY

It is an object of the present disclosure to provide a state estimation device and a state estimation program, which estimate a state of a monitoring target, and to estimate the state of a monitoring target in a shorter time with the state estimation device.

According to one aspect of the present disclosure, a state estimation device estimating a state of a monitoring target based on an involuntary eye movement of an eyeball of the monitoring target is provided. The state estimation device includes a microsaccade information acquisition portion obtaining microsaccade information that includes a state of variation of a gaze angle when a microsaccade of the involuntary eye movement occurs, and a state estimation portion estimating the state of the monitoring target based on the microsaccade information.

According to the state estimation device in the present disclosure, the state of the monitoring target is estimated using the microsaccade information including the state of variation of the gaze angle when the microsaccade occurs, and it is possible to estimate the state of the monitoring target in a short time.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Embodiments according to the present disclosure will be explained with referring to the drawings.

(Configuration of Present Embodiment)

An attention estimation system 1, which is a system, in the present disclosure is mounted to a vehicle (also referred to as a subject vehicle) such as a passenger vehicle or the like, recognizes whether a state of a driver (also referred to as an operator, or a monitoring target) is in a state (an attention insufficient state) where the driver lacks an attention, based on an involuntary eye movement of an eyeball of the driver, who is a monitoring target, and when the state of the driver is a lack of the attention (that is, in a case where the driver is in the attention insufficient state), perform an alarm.

Figure 1:
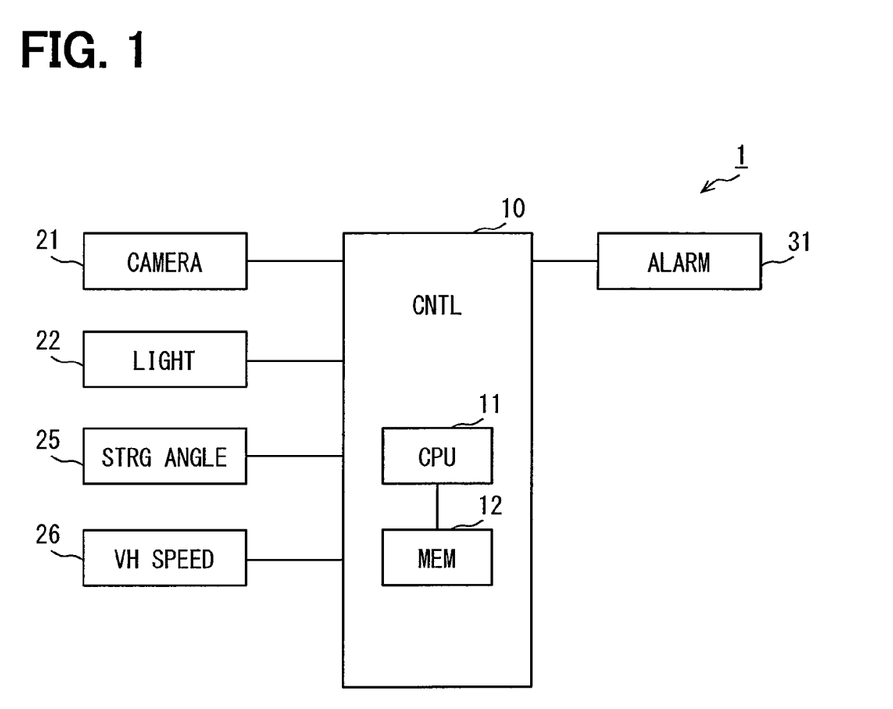
FIG. 1 is a block diagram illustrating a schematic configuration of an attention estimation system to which a present disclosure is applied.

In detail, the attention estimation system 1 includes a controller 10, a camera 21, an illumination part 22, a steering angle sensor 25, a speed sensor 26, and an alarm section 31, as illustrated in FIG. 1.

The camera 21 is arranged in front of the driver in the interior of a vehicle, and is set up so that the eyeball of the driver is included in an imaging range of the camera 21. For example, the camera 21 is arranged in the interior of a goggles mounted by the driver. The camera 21 is set up so that a positional relationship between the eyeball and the camera 21 may not be changed according to a movement of a face of the driver.

Incidentally, the camera 21 may not be arranged as described above as long as the camera 21 is configured to image a fine motion (e.g. an angle of the eyeball) of the eyeball. For example, the camera 21 may be arranged so that a whole face of the monitoring target is included within an imaged picture of the camera 21. The camera 21 is a high-speed and high precision camera. The camera 21 images in a cycle (for example, a frame rate about 200 fps) and with a precision (for example, a precision detecting an angle difference of 0.05 degree), and detects the involuntary eye movement (i.e. a microsaccade) of the eyeball of the driver. Incidentally, about 200 fps means about 200 frames per second.

The illumination part 22 functions as an assisting light source for the camera 21, and irradiates with, for example, infrared ray towards the face of the driver corresponding to the imaging range of the camera 21. With respect to an irradiation timing of the infrared ray, the illumination part 22 may turn on continuously, or the illumination part 22 may be controlled so that the irradiation timing is synchronized with an imaging period with the camera 21.

The steering angle sensor 25 is a sensor detecting a steering wheel position by a steering wheel operation by the driver, and corresponds to a well-known steering angle sensor. The steering angle detected by the steering angle sensor 25 is configured to be recognized by the controller 10.

The speed sensor 26 is a well-known speed sensor detecting a travelling speed of the subject vehicle. The speed sensor 26 sends a detection result of the vehicle speed to the controller 10.

The alarm portion 31 is a configuration for calling an attention to the driver with sound or light, and is operated in response to an instruction from the controller 10. Incidentally, when the alarm portion 31 receives the instruction from the controller 10, the alarm portion 31 may perform an alarm by operating a vibrator embedded on a driver's sheet, or when the alarm portion 31 receives the instruction from the controller 10, the alarm portion 31 may perform an alarm by changing an air amount, an wind direction, and a preset temperature of an air conditioner in the vehicle.

The controller 10 is configured as a well-known computer having a CPU 11, and a memory 12 such as a ROM, a RAM, or the like. The CPU 11 performs various processing according to a program stored on the memory 12.

(Processing of Present Embodiment)

In the attention estimation system 1, the controller 10 performs an attention estimation processing illustrated in FIG. 2 and the following drawings. The attention estimation processing is a processing started when, for example, a power source of the attention estimation system 1 turns on. The attention estimation processing is repeatedly performed for each constant period after starting.

Figure 2A:
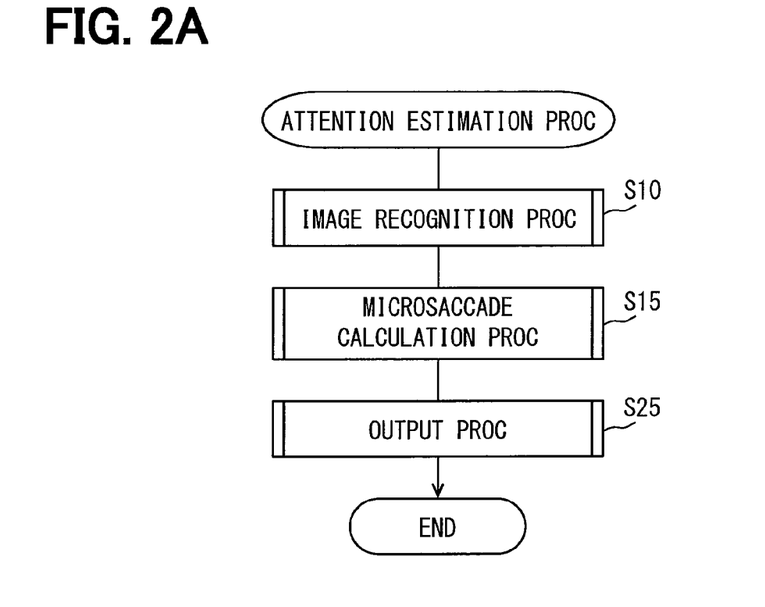
FIG. 2A is a flowchart illustrating the attention estimation processing executed by a controller (CPU)

In the attention estimation processing, as illustrated in FIG. 2A, an image recognition processing is performed initially (S10). In the image recognition processing, a fine motion of the eyeball of the driver (also referred to as the monitoring target) is detected from the imaged picture obtained by the camera 21.

Figure 3:
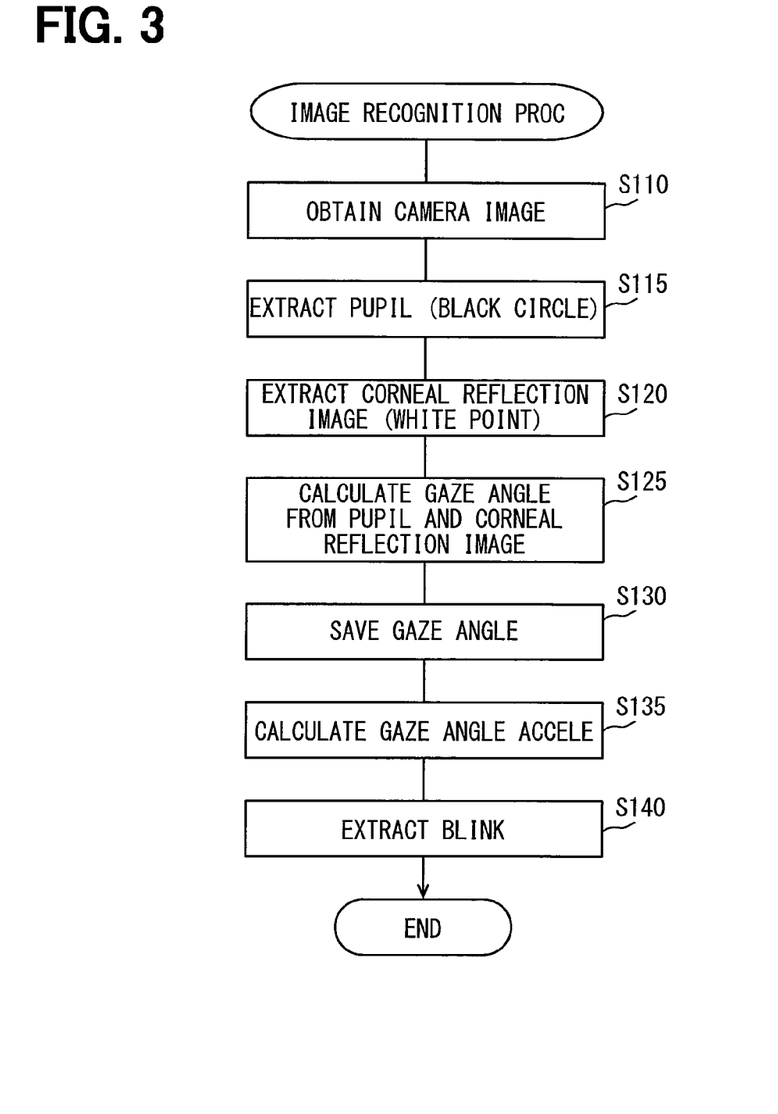
FIG. 3 is a flowchart illustrating an image recognition processing in the attention estimation processing.

The image recognition processing obtains the imaged picture by the camera 21 initially, as illustrated in FIG. 3 (S110). The image recognition processing extracts a pupil in the imaged picture (S115). In the image recognition processing, the black circle in the imaged picture is extracted as the pupil. Incidentally, when the camera 21 is arranged so that the whole face of the monitoring target is included in the imaged picture, a position of the eyeball in the imaged picture is detected, the black circle in the eyeball is extracted as the pupil, and the position of the pupil is recorded.

A corneal reflection image is extracted (S120). The corneal reflection image corresponds to a reflected light that the light from the light source is reflected by a cornea in the pupil. The corneal reflection image is expressed as a white point in the imaged picture. The position of the white point is recorded.

The controller 10 calculates a gaze angle (also referred to as an eye position) according to a positional relationship (e.g. each position and each angle of the pupil and the corneal reflection image, a relative distance between the pupil and the corneal reflection image, or the like) of positions of the pupil and the corneal reflection image (S125). Herein, the gaze angle means a horizontal direction, which is generally matched with a right-and-left direction of the vehicle, and a perpendicular direction, which is perpendicular to the horizontal direction.

The controller 10 stores the gaze angle calculated at S125 in the memory 12 (S130), and calculates a gaze angle acceleration (S135). By using the gaze angles corresponding to past several frames stored in the memory 12, the gaze angle acceleration is calculated by dividing a variation amount of the gaze angle by time. The past several frames correspond to frames that are enough to calculate the gaze angle acceleration, and correspond to ten frames, for example.

The controller 10 also extracts a blink (palpebration) (S140). With respect to the blink, for example, when the pupil is not extracted, it is considered that the blink is performed. Alternatively, the blink may be determined based on a curvature radius of an upper eyelid.

The time with respect to the blink is recorded on the memory 12. After the processing of S140 is terminated, the image recognition processing ends.

A microsaccade calculation processing is performed (S15 in FIG. 2A). The microsaccade calculation processing is a processing calculating a parameter for estimating an attention of the driver with respect to the microsaccade by the driver.

Figure 4:
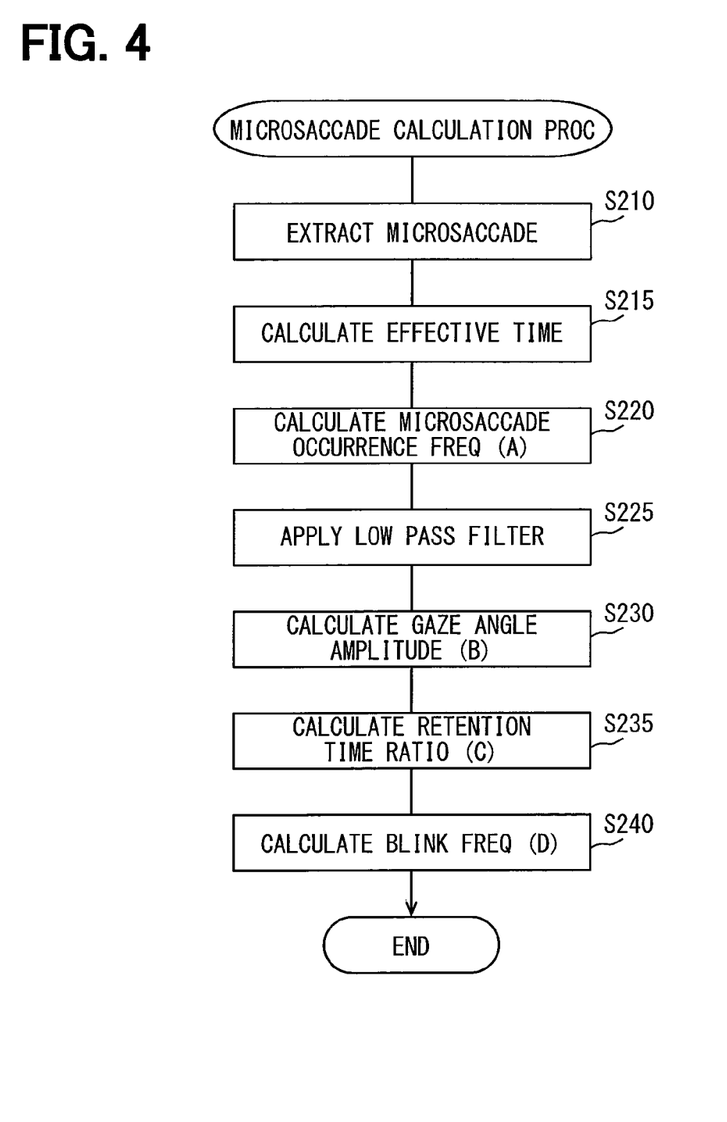
FIG. 4 is a flowchart illustrating a microsaccade calculation processing in the attention estimation processing.

In the microsaccade calculation processing, as illustrated in FIG. 4, the microsaccade is extracted initially (S210). In the processing, when the gaze angle acceleration is equal to or more than a reference angle rate and a movement distance of the gaze is less than a reference distance (that is, the two conditions are satisfied), it is considered that the microsaccade occurs. The reference angle rate is 1200 deg/s$^2$, for example. The movement distance of the gaze is a difference of the gaze angle after the variation of the gaze angle begins until the variation of the gaze angle stops. The reference distance corresponds to 2 degrees, for example.

That is, in the microsaccade calculation processing, it is considered that the microsaccade, which is extracted, occurs in a case where the variation of the gaze angle is small enough to an extent that the driver does not intend and the gaze angle velocity is large.

Followingly, an effective time is calculated (S215). Herein, the effective time corresponds to a time except a predetermined time before or after the blink. The predetermined time corresponds to a time (for example, each 200 milliseconds before or after the blink) when the eyeball moves in the blink.

A microsaccade occurrence frequency (A) is calculated (S220). In the processing, the number of times of the microsaccade occurrence within a constant time (for example, for 30 seconds, or the like) is counted, and a microsaccade occurrence frequency (A) is calculated by dividing the number of times by the effective time, which is included in the constant time.

Followingly, a low pass filter is applied to the gaze angle (for example, the gaze angle within the effective time) except before or after the blink (S225). A value applied with the low pass filter on the gaze angle is used as an amplitude reference origin (i.e. zero point) at the time of calculating amplitude of the gaze angle.

A gaze angle amplitude (B) after the microsaccade occurrence is calculated (S230). The gaze angle amplitude (B) means a difference between the amplitude reference origin and an angle when the microsaccade occurs and a gaze movement stops.

A retention time ratio (C) is calculated (S235). In the processing, the retention time ratio (C) is obtained by dividing a gaze retention time after the occurrence of the microsaccade by the gaze angle amplitude. The gaze retention time after the occurrence of the microsaccade corresponds to a time after the gaze movement stops when the microsaccade occurs and before the next gaze movement begins.

A blink frequency (D) is calculated (S240). The blink frequency is calculated by counting the time of the blinks within a constant time (for example, for 30 seconds, or the like).

When the processing is terminated, the microsaccade calculation processing is terminated. An example of the variation of the gaze angle according to time will be illustrated by a graph, as illustrated in FIGS. 5A and 5B.

Figure 5A:
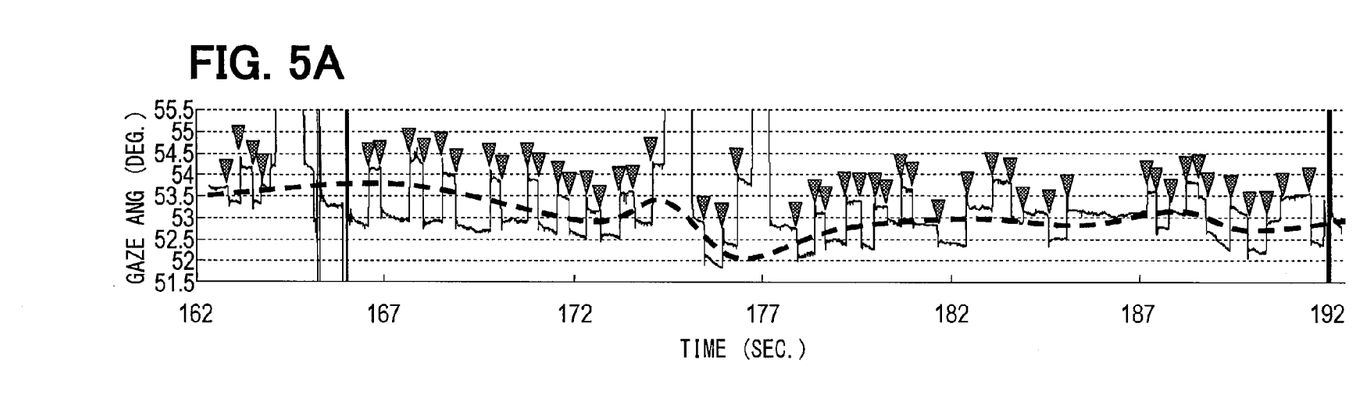
FIG. 5A is a graph illustrating a temporal change of a gaze angle at the time of a microsaccade occurrence.
Figure 5B:
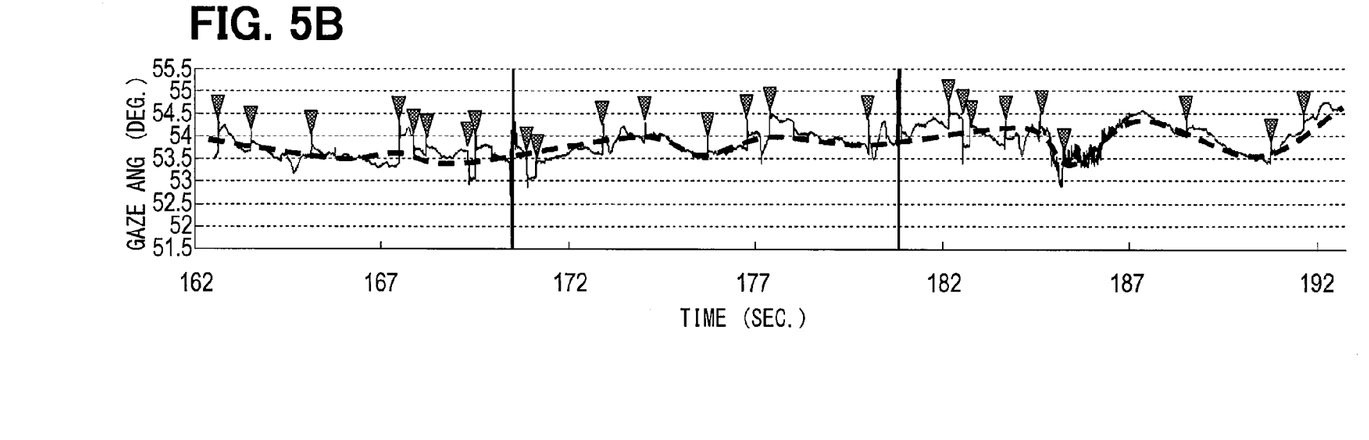
FIG. 5B is a graph illustrating a temporal change of a gaze angle at the time of a microsaccade occurrence.

Incidentally, in the example described in FIG. 5A and FIG. 5B, a downward triangle illustrates a position when the microsaccade occurs. In addition, a broken line in FIG. 5A and FIG. 5B illustrates the amplitude reference origin (also referred to as a gaze movement average).

In order to obtain a graph illustrated in FIG. 5A and FIG. 5B, the same test subject is caused to perform a simulation driving using a driving simulator. FIG. 5A illustrates a result (corresponding to the attention sufficient state) obtained when the test subject is focused on driving without requiring another task (for example, making a mental arithmetic or the like) in the simulation driving. On the contrary, FIG. 5B illustrates a result (corresponding to the attention insufficient state) obtained when the test subject is required to perform another task (for example, making a mental arithmetic or the like) during driving in the simulation driving.

As illustrated in FIG. 5A, when the attention of the driver (i.e. the test subject) is enough, a microsaccade occurrence frequency (A) is high and the gaze angle amplitude (B) is large as compared with a case where the attention of the driver is insufficient.

When the attention of the driver is sufficient, the retention time ratio (C) tends to become small as compared with the case where the attention of the driver is insufficient. When the attention of the driver is sufficient, the blink frequency (D) tends to become many as compared with the case where the attention of the driver is insufficient.

The applicants have found the above described tendency. An output processing in FIG. 2A will be explained using the tendency (S25). The output processing is a processing estimating the state of the driver by comparing calculated parameters (e.g. the microsaccade occurrence frequency, the gaze angle amplitude, the retention time ratio, the blink frequency, or the like) with thresholds, and outputting a result (e.g. an alarm).

Figure 6:
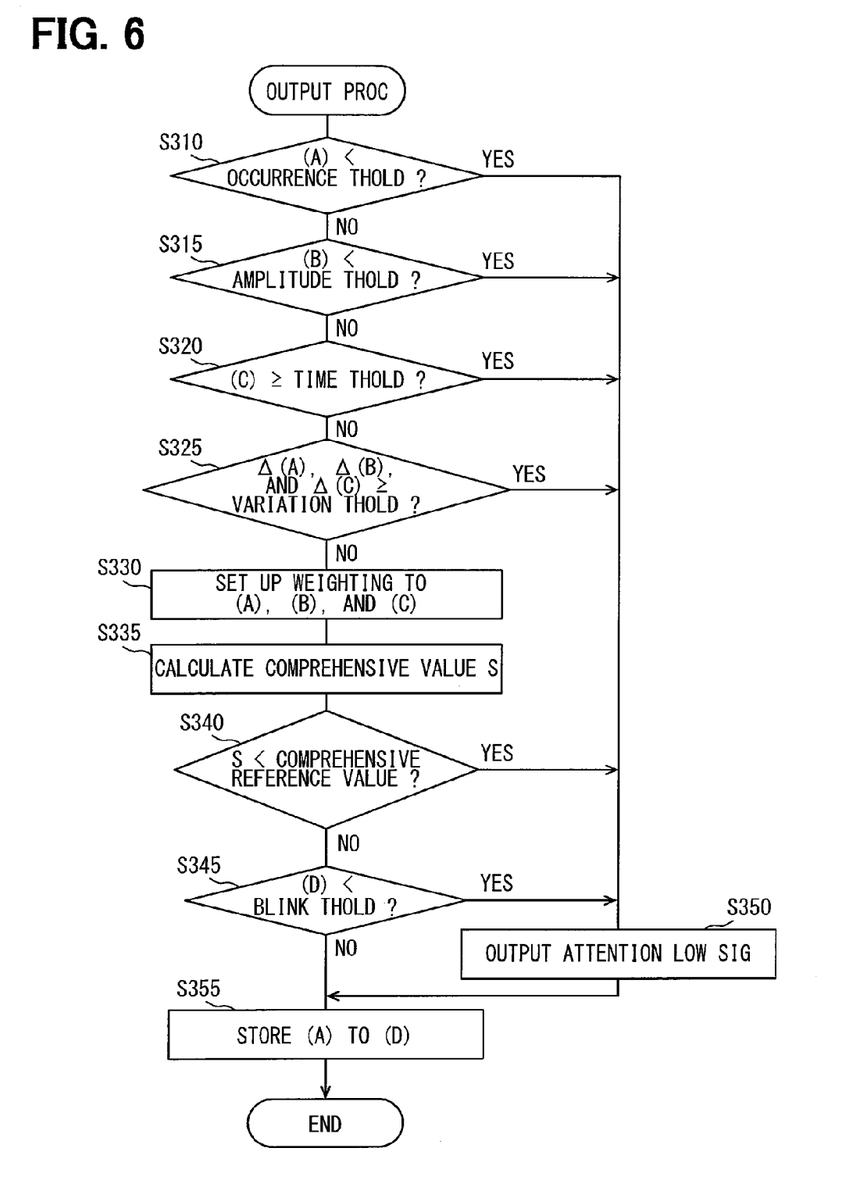
FIG. 6 is a flowchart illustrating an output processing in the attention estimation processing in the present embodiment.

The output processing compares the microsaccade occurrence frequency (A) with a predetermined occurrence threshold (S310) initially. Thresholds in the present processing or the following processing is set to a middle value of an average value (corresponding to the microsaccade occurrence frequency) of a person with a sufficient attention and an average value of a person with an insufficient attention.

When the microsaccade occurrence frequency (A) is less than the occurrence threshold (S310: YES), the processing moves to S350. When the microsaccade occurrence frequency (A) is equal to or more than the occurrence threshold (S310: NO), the gaze angle amplitude (B) is compared with a predetermined amplitude threshold (S315).

When the gaze angle amplitude (B) is less than the amplitude threshold (S315: YES), the processing moves to S350. When the gaze angle amplitude (B) is equal to or more than the amplitude threshold (S315: NO), the retention time ratio (C) is compared with a predetermined time threshold (S320).

When the retention time ratio (C) is equal to or more than time threshold (S320: YES), the processing moves to S350. When the retention time ratio (C) is less than the time threshold (S320: NO), the processing moves to S325. At S325, each rate of change of the microsaccade occurrence frequency (A), the gaze angle amplitude (B), and the retention time ratio (C) is compared with each predetermined variation threshold. For example, each rate of change corresponds to a variation magnitude between each value or an average value from 20 seconds before to 10 seconds before, and each value or an average value from 10 seconds before to the present. The rates of change of the microsaccade occurrence frequency (A), the gaze angle amplitude (B), and the retention time ratio (C) are expressed as Δ(A), Δ(B), Δ(C), respectively in FIG. 6 and FIG. 7.

When the rates of change of the microsaccade occurrence frequency (A), the gaze angle amplitude (B), and the retention time ratio (C) are equal to or more than the variation thresholds (S325: YES), the processing moves to S350. When the rates of change of the microsaccade occurrence frequency (A), the gaze angle amplitude (B), and the retention time ratio (C) are less than the variation thresholds (S325: NO), weighting to the microsaccade occurrence frequency (A), the gaze angle amplitude (B), and the retention time ratio (C) is set up (S330).

When setting up the weighting to the microsaccade occurrence frequency (A), the gaze angle amplitude (B), and the retention time ratio (C), factors W1, W2, and W3 are set up to the microsaccade occurrence frequency (A), the gaze angle amplitude (B), and the retention time ratio (C), respectively. The factors W1, W2, and W3 are set up arbitrarily according to which of the microsaccade occurrence frequency (A), the gaze angle amplitude (B), and the retention time ratios (C) is focused on.

A comprehensive value S is calculated (S335). The comprehensive value S is obtained by multiplying the microsaccade occurrence frequency (A) by W1, multiplying the gaze angle amplitude (B) by W2, and multiplying the retention time ratio (C) by W3, and by adding the weighted values.

The comprehensive value S is compared with a predetermined comprehensive reference value (S340). The comprehensive reference value corresponds to a middle value of the comprehensive value S when a person is in the insufficient attention and the comprehensive value S when a person is in the sufficient attention considering a tendency of the both comprehensive values S.

When the comprehensive value S is less than the comprehensive reference value (S340: YES), the processing moves to S350. When the comprehensive value S is equal to or more than the comprehensive reference value (S340: NO), a blink frequency (D) is compared with a predetermined blink threshold (S345).

When the blink frequency (D) is less than the blink threshold (S345: YES), an attention lowering signal is outputted (S350) and the processing moves to S355. The attention lowering signal corresponds to a signal outputted to the outside of the controller 10, for example, outputted to an alarm portion 31. The alarm portion 31 performs an alarm to the driver when the attention lowering signal is received.

When the blink frequency (D) is equal to or more than the blink threshold (S345: NO), the microsaccade occurrence frequency (A), the gaze angle amplitude (B), the retention time ratio (C), and the blink frequency (D) are recorded on the memory 12 (S355), and the output processing is terminated. The attention estimation processing ends when the output processing ends.

In the attention estimation system 1 of the present disclosure, the controller 10 (e.g. CPU 11) obtains microsaccade information including a state of variation of the gaze angle when the microsaccade of the involuntary eye movements occurs, and estimates a state of the monitoring target based on the microsaccade information.

According to the attention estimation system 1, since the state of the monitoring target is estimated using the microsaccade information including the state of variation of the gaze angle when the microsaccade occurs, it is possible to estimate the state of the monitoring target in a short time.

The inventors of the present disclosure have found that, when the state of the monitoring target is in a good condition, an amplitude of the gaze angle when the microsaccade occurs becomes comparatively large, and when the state of the monitoring target is in a bad condition such as a case where the attention is lacked or the like, the amplitude of the gaze angle when the microsaccade occurs becomes comparatively small.

Therefore in the present disclosure, the controller 10 estimates the state of the monitoring target based on the amplitude of the gaze angle when the microsaccade occurs. Especially, it is estimated that the attention of the monitoring target is in a high state as the amplitude becomes large. On the contrary, it is estimated that the attention of the monitoring target is in a low state as the amplitude becomes small. In other words, when the attention is in the high state, the monitoring target has a high attention, and when the attention is in the low state, the monitoring target has a low attention.

According to the attention estimation system 1, it is possible to estimate a state (also referred to as an attention insufficient state) that the monitoring target does not look at an object with attention although a gaze direction of the monitoring target goes to the object, using a simple algorithm.

In addition, in the attention estimation system 1, the controller 10 calculates the amplitude on the basis of the movement average of the gaze angle.

According to the attention estimation system 1, since the movement average (corresponding to an average value of the gaze angle within a latest past reference time) of the gaze angle is used as a reference, it is possible to calculate the amplitude with a simple configuration.

In addition, the inventers of the present disclosure have also found that, when the state of the monitoring target is in the good condition, the retention time of the gaze angle after the microsaccade becomes comparatively long, and when the state of the monitoring target is in the bad condition, the retention time of the gaze angle when the microsaccade occurs becomes comparatively short. In addition, the inventers of the present disclosure have found that there is a remarkable tendency about the retention time ratio obtained by dividing the retention time by the amplitude.

Therefore in the present disclosure, the controller 10 estimates the state of the monitoring target based on the retention time (the retention time ratio) of the gaze angle when the microsaccade occurs. Especially, it is estimated that the attention of the monitoring target is in the high state as the retention time becomes long, and on the contrary, it is estimated that the attention of the monitoring target is in the low state as the retention time becomes short.

According to the attention estimation system 1, since the retention time (the retention time ratio) is also considered in addition to the state of variation of the gaze angle, it is possible to estimate the state of the monitoring target more precisely.

In addition, the controller 10 in the present disclosure estimates the state of the monitoring target considering the frequency of the blink. Especially, it is estimated that the attention of the monitoring target is in the high state as the blink frequency becomes high, and on the contrary, it is estimated that the attention of the monitoring target is in the low state as the blink frequency becomes low.

According to the attention estimation system 1, since the blink frequency is also considered in addition to the state of variation of the gaze angle, it is possible to estimate the state of the monitoring target more precisely.

In addition, the controller 10 in the attention estimation system 1 obtains an occurrence frequency of the microsaccade as the microsaccade information, and estimates the state of the monitoring target considering the occurrence frequency. Especially, it is estimated that the attention of the monitoring target is in the high state as the microsaccade occurrence frequency becomes high, and on the contrary, it is estimated that the attention of the monitoring target is in the low state as the microsaccade occurrence frequency becomes low.

According to the attention estimation system 1, since the microsaccade information includes the microsaccade occurrence frequency, it is possible to estimate the state of the monitoring target with high precision using more microsaccade information.

The controller 10 in the attention estimation system 1 estimates as the state of the monitoring target a level of the attention to a visual recognition object included in the gaze direction of the monitoring target.

According to the attention estimation system 1, it is possible to estimate whether the monitoring target concentrates and looks at the visual recognition object or not.

In addition, the controller 10 in the attention estimation system 1 performs an alarm according to the state of the monitoring target. Especially, the controller 10 performs the alarm when it is determined that the attention is lowered.

According to the attention estimation system 1, since the alarm is performed, it is possible to notify the monitoring target that the monitoring target is in the bad state (that is, the state of the monitoring target is not in the good state). It is possible to improve the state of the monitoring target.

The controller 10 in the attention estimation system 1 is mounted to a vehicle, and is configured to estimate the state of the driver of the vehicle as the monitoring target.

According to the attention estimation system 1, since the state of the attention of the driver of the vehicle is estimated, it may be possible to prevent a traffic trouble by a careless driving.

(Modification)

The present disclosure is not limited to the embodiment described above. It should be noted that the embodiment of the present disclosure includes aspects, in which a part of the configurations of the present embodiment is omitted, as long as a subject of the present disclosure is solved. In addition, embodiments in the present disclosure include aspects obtained by appropriately combining two or more embodiments. In addition, it should be noted that any aspect is included in embodiments of the present disclosure within a technical scope of the present disclosure specified by the description in the present disclosure.

For example, in the embodiment, the present disclosure is applied to the vehicle. However, the present disclosure is not limited to the vehicle, and may be applicable to any condition where the state of the monitoring target is required to be estimated. In the embodiment, the retention time ratio is used when the state of the monitoring target is estimated. However, another parameter such as a retention time or the like may be used for estimating the state of the monitoring target.

In addition, in the present embodiment, each threshold value is set up based on the average value of a general monitoring target. However, information with respect to the microsaccade of individual monitoring target may be stored on a database, and each threshold value may be changed and set up according to the individual monitoring target based on the database.

In addition, in the present embodiment, the state of the monitoring target is evaluated on a two level scale: good, and bad. The state of the monitoring target may be evaluated on a multiple level scale. In this case, the evaluation may be performed considering a tendency that the microsaccade information increases or decreases as the state of the monitoring target becomes good.

The controller 10 in the attention estimation system 1 may obtain a vehicle parameter illustrating a travelling state or a travelling circumstance of a vehicle, and may correct the microsaccade information based on the vehicle parameter.

Figure 2B:
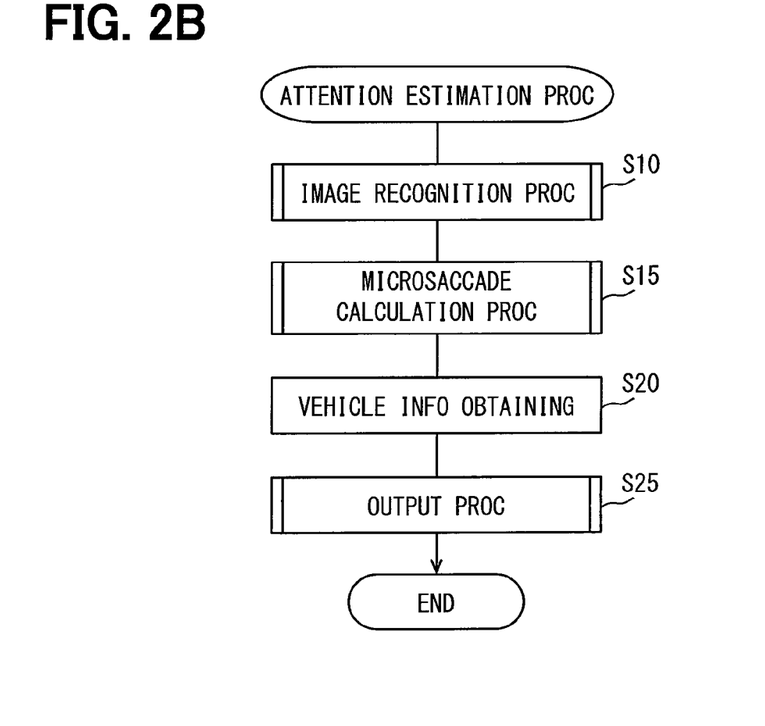
FIG. 2B is a flowchart illustrating the attention estimation processing executed by a controller (CPU)
Figure 7:
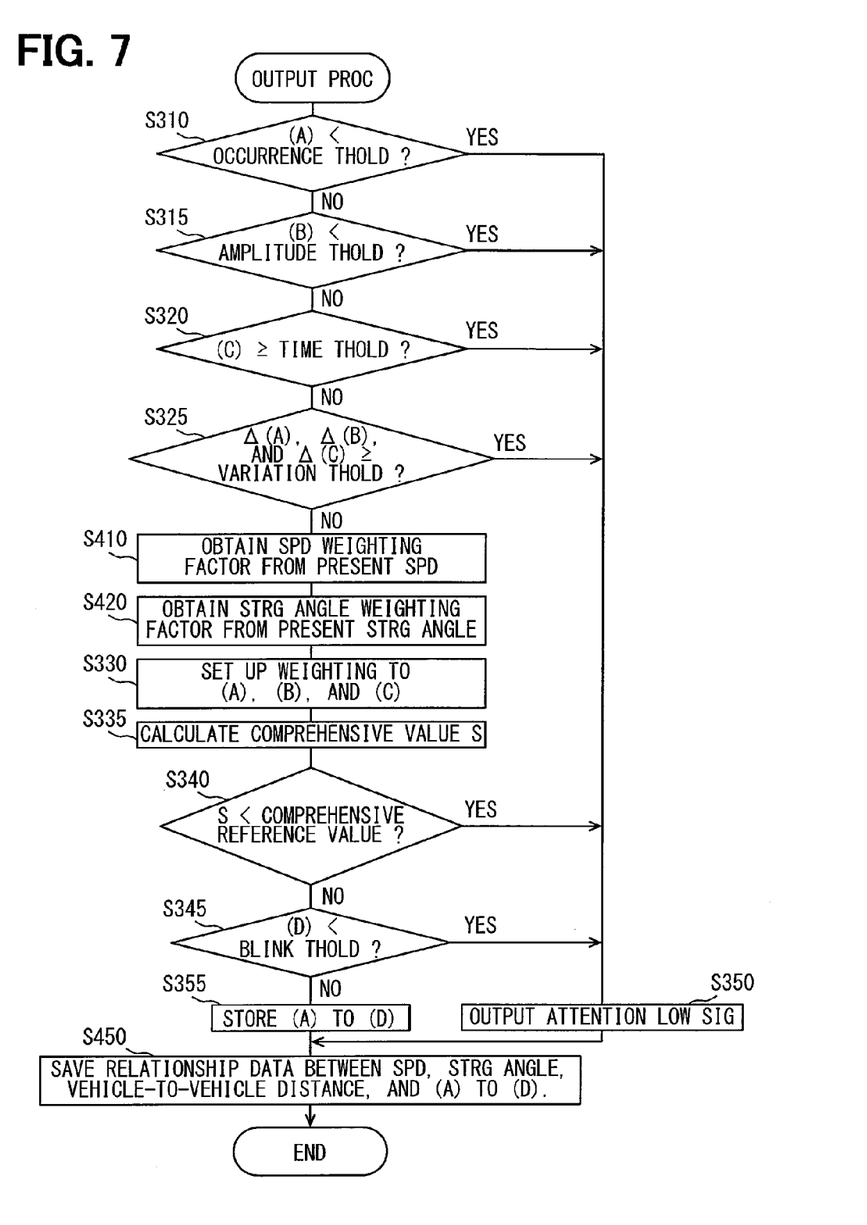
FIG. 7 is a flowchart illustrating an output processing in the attention estimation processing in a modification.

Specifically, as described in FIG. 2B, the vehicle information may be obtained (S20) between S15 and S25, and a processing corresponding to S410 and S420 may be performed between the processing of S325 and S330, as illustrated in FIG. 7. Herein, the vehicle information includes a travelling state of the vehicle such as a steering angle, a vehicle speed, or the like, and a travelling circumstance such as a surrounding brightness, a road state, or the like.

In addition, in the processing of S410 and S420, a speed weighting factor Wa based on the vehicle speed and a steering angle weighting factor Wb based on the steering angle are set up. Incidentally, the speed weighting factor Wa is set up to decrease as the vehicle speed increases, and the steering angle weighting factor Wb based on the steering angle is set up to increase as the steering angle increases.

At S450, a relationship data is stored in the memory 12 or the like. The relationship data represents a relationship between a vehicle speed, a steering angle, a vehicle-to-vehicle distance, the microsaccade occurrence frequency (A), the gaze angle amplitude (B), the retention time ratio (C), and the blink frequency (D).

In the processing of S335, the calculated comprehensive value S is multiplied by each of the factors Wa, Wb, consecutively to obtain a new comprehensive value S, and the new comprehensive value S is used in the following processing.

According to the attention estimation system 1 in the modification, it may be possible that the attention estimation system 1 easily determines that the attention of the monitoring target is in the bad state in a case where the attention of the monitoring target may be easily lacked according to the vehicle parameters, and the attention estimation system 1 easily determines that the attention of the monitoring target is in the good state in a case where the attention is not easily lacked.

In the present embodiment, the amplitude is applied as a specific example of the state of variation of the gaze angle when the microsaccade occurs. However, a value other than the amplitude may be applied.

The controller 10 corresponds to a state estimation device in the present disclosure. The processing of S15 of the processing executed by the controller 10 corresponds to a microsaccade information acquisition portion in the present embodiment. The processing of S25 corresponds to a state estimation portion in the present disclosure.

The processing of S240 corresponds to a blink frequency acquisition portion in the present disclosure. The processing of S350 corresponds to an alarm portion in the present disclosure. The processing of S410 and S420 corresponds to a vehicle parameter acquisition portion in the present disclosure. The processing of S330 corresponds to a microsaccade information correction portion in the present disclosure.

According to one aspect of the present disclosure, a microsaccade information acquisition portion in the state estimation device obtains microsaccade information including a state of variation of a gaze angle when a microsaccade of the involuntary eye movement occurs. The state estimation portion estimates the state of the monitoring target based on the microsaccade information.

According to the state estimation device, since the state of the monitoring target is estimated using the microsaccade information including the state of variation of the gaze angle when the microsaccade occurs, it is possible to estimate the state of the monitoring target in a short time.

Incidentally, a state estimation program may cause a computer to function as each portion configuring the state estimation device. In addition, a description of the present disclosure may be arbitrarily combined each other as much as possible. In this case, it may be possible to partially omit within a scope to achieve a subject of the present disclosure.

It is noted that a flowchart or the processing of the flowchart in the present application includes sections (also referred to as steps), each of which is represented, for instance, as S10. Further, each section can be divided into several sub-sections while several sections can be combined into a single section. Furthermore, each of thus configured sections can be also referred to as a device, module, or means.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. A state estimation device estimating a state of a monitoring target person based on an involuntary eye movement of an eyeball of the monitoring target person, the state estimation device comprising:
a microsaccade information acquisition portion obtaining microsaccade information that includes a state of variation of a gaze angle when a microsaccade of the involuntary eye movement occurs; and
a state estimation portion estimating the state of the monitoring target person based on the microsaccade information,
wherein:
the microsaccade has a gaze angle acceleration being equal to or more than a reference angle rate and also has a different of the gaze angle before and after the variation of the gaze angle being less than a reference distance.

2. The state estimation device according to claim 1, wherein
the state estimation portion estimates the state of the monitoring target person based on amplitude of the gaze angle when the microsaccade occurs.

3. The state estimation device according to claim 2, wherein
the state estimation portion estimates that an attention of the monitoring target person is low as the amplitude of the gaze angle is small.

4. The state estimation device according to claim 2, wherein
the state estimation portion calculates the amplitude of the gaze angle on a basis of a movement average of the gaze angle.

5. The state estimation device according to claim 1, wherein
the microsaccade information acquisition portion obtains a retention time of the gaze angle after the microsaccade as the microsaccade information, and
the state estimation portion estimates the state of the monitoring target person considering the retention time.

6. The state estimation device according to claim 5, wherein
the state estimation portion estimates that the attention of the monitoring target person is low as the retention time is short.

7. The state estimation device according to claim 1 further comprising
a blink frequency acquisition portion obtaining a frequency of a blink of the monitoring target person, wherein
the state estimation portion estimates the state of the monitoring target considering the frequency of the blink.

8. The state estimation device according to claim 7, wherein
the state estimation portion estimates that the attention of the monitoring target person is low as the frequency of the blink of the monitoring target person is low.

9. The state estimation device according to claim 1, wherein
the microsaccade information acquisition portion obtains an occurrence frequency of the microsaccade as the microsaccade information, and
the state estimation portion estimates the state of the monitoring target person considering the occurrence frequency.

10. The state estimation device according to claim 9, wherein
the state estimation portion estimates that the attention of the monitoring target person is low as the occurrence frequency is low.

11. The state estimation device according to claim 1, wherein
the state estimation portion estimates a level of the attention of the monitoring target person to a visual recognition object included in a gaze direction of the monitoring target person as the state of the monitoring target person.

12. The state estimation device according to claim 1 further comprising
an alarm portion performing an alarm according to the state of the monitoring target person.

13. The state estimation device according to claim 1, wherein
the state estimation device is mounted to a vehicle,
a driver of the vehicle corresponds to the monitoring target person, and
the state estimation device estimates a state of the driver of the vehicle.

14. The state estimation device according to claim 13 further comprising
a vehicle parameter acquisition portion obtaining a vehicle parameter that expresses a travelling state of the vehicle, and
a microsaccade information correction portion correcting the microsaccade information based on the vehicle parameter.

15. A state estimation program causing a computer to perform a function of the microsaccade information acquisition portion or the state estimation portion configuring the state estimation device according to claim 1.

16. A non-transitory computer readable storage medium storing the state estimation program according to claim 15.

17. The state estimation device according to claim 1, further comprising
an alarm portion performing an alarm according to the state of the monitoring target person,
wherein:
the state estimation portion estimates the state of the monitoring target person based on amplitude of the gaze angle when the microsaccade occurs;
the microsaccade information acquisition portion obtains a retention time of the gaze angle after the microsaccade as the microsaccade information;
the state estimation portion estimates the state of the monitoring target person by also considering the retention time;
the microsaccade information acquisition portion also obtains an occurrence frequency of the microsaccade as the microsaccade information; and
the state estimation portion estimates the state of the monitoring target person by also considering the occurrence frequency.

18. The state estimation device according to claim 1, wherein:
the reference angle rate is equal to 1200 deg/s$^2$; and
the reference distance is equal to 2 degrees.

* * * * *